(12) United States Patent
Park et al.

(10) Patent No.: US 11,298,023 B2
(45) Date of Patent: Apr. 12, 2022

(54) PERSONALIZED OPTIMAL HEAD SHAPE IMPLEMENTATION SYSTEM

(71) Applicant: SECRETWOMAN CO., LTD., Daejeon (KR)

(72) Inventors: Se Jin Park, Anseong-si (KR); Seung Hee Hong, Daejeon (KR); Murali Subramaniyam, Daejeon (KR); Young Hyu Kim, Daejeon (KR)

(73) Assignee: SECRETWOMAN CO., LTD., Daejeon (KR)

( * ) Notice: Subject to any disclaimer, the term of this patent is extended or adjusted under 35 U.S.C. 154(b) by 225 days.

(21) Appl. No.: 16/486,117

(22) PCT Filed: Feb. 14, 2018

(86) PCT No.: PCT/KR2018/001957
§ 371 (c)(1),
(2) Date: Aug. 14, 2019

(87) PCT Pub. No.: WO2018/151543
PCT Pub. Date: Aug. 23, 2018

(65) Prior Publication Data
US 2020/0229700 A1 Jul. 23, 2020

(30) Foreign Application Priority Data
Feb. 14, 2017 (KR) .......................... 10-2017-0020151

(51) Int. Cl.
*A61B 5/00* (2006.01)
*A61B 5/107* (2006.01)

(52) U.S. Cl.
CPC ............ *A61B 5/0064* (2013.01); *A61B 5/742* (2013.01); *A61B 5/0077* (2013.01); *A61B 5/1072* (2013.01); *A61B 5/7264* (2013.01); *A61B 5/7278* (2013.01)

(58) Field of Classification Search
CPC ....... A61B 5/00; A61B 5/0064; A61B 5/0077; A61B 5/107; A61B 5/1072; A61B 5/1075;
(Continued)

(56) References Cited

U.S. PATENT DOCUMENTS 6,340,353 B1 * 1/2002 Pomatto .............. A61F 5/05891
602/17
6,810,597 B2 * 11/2004 Grzesiak .............. G01B 21/042
33/503
(Continued)

FOREIGN PATENT DOCUMENTS

KR 10-0645976 B1 11/2006
KR 10-0889240 B1 3/2009
(Continued)

OTHER PUBLICATIONS

International Search Report of corresponding PCT Application No. PCT/KR2018/001957—2 pages (dated May 1, 2018).

*Primary Examiner* — Christian Jang
*Assistant Examiner* — Anna Roberts
(74) *Attorney, Agent, or Firm* — Knobbe Martens Olson & Bear LLP (57) ABSTRACT

A personalized optimal head shape implementation system capable of deriving an optimal spline curve between head shape measurement data generated by scanning a head shape of a subject and optimal head shape data generated by applying a golden ratio of a Fibonacci sequence to the head shape measurement data and providing a customized optimal head shape mold for the subject based on the optimal spline curve.

2 Claims, 13 Drawing Sheets

(58) Field of Classification Search
CPC ... A61B 5/1077; A61B 5/1079; A61B 5/6814; A61B 5/7264; A61B 5/7278; A61B 5/742; A61B 5/743; G16H 50/20
USPC .......................................................... 600/587
See application file for complete search history.

(56) References Cited

U.S. PATENT DOCUMENTS

2012/0296249 A1   11/2012  Gordon et al.
2015/0206339 A1*   7/2015  Chun .................... G06T 15/205
                                                                345/419

FOREIGN PATENT DOCUMENTS

| KR | 10-1495810 B1 | 2/2015 |
| KR | 10-1675400 B1 | 11/2016 |
| KR | 10-1702774 B1 | 2/2017 |
| KR | 101702774 B1 * | 2/2017 |

* cited by examiner

DESIGN THAT DOES NOT GIVE USER UNPLEASANTNESS
ADJUST HEIGHT

| 1 | NOSE HEIGHT | 24 | MENTUM OCCIPUT PROTRUSION HORIZONTAL LENGTH |
|---|---|---|---|
| 2 | NOSE LENGTH | 25 | ROOT OF NOSE OCCIPUT PROTRUSION HORIZONTAL LENGTH |
| 3 | HEAD CIRCUMFERENCE | 26 | ROOT OF NOSE AURICLE RADIX SUPERIOR HORIZONTAL LENGTH |
| 4 | HEAD VERTICAL LENGTH | 27 | RIGHT TRAGUS OCCIPUT PROTRUSION HORIZONTAL LENGTH |
| 5 | VERTEX_LOWER JAW BONE VERTICAL LENGTH | 28 | LEFT TRAGUS OCCIPUT PROTRUSION HORIZONTAL LENGTH |
| 6 | VERTEX_RIGHT TRAGION VERTICAL LENGTH | 29 | CROW TRAGUS HORIZONTAL LENGTH |
| 7 | VERTEX_LEFT TRAGION VERTICAL LENGTH | 30 | TRAGUS LIP LINEAR LENGTH |
| 8 | VERTEX_LIP VERTICAL LENGTH | 31 | GLABELLA VERTEX OCCIPUT (ARC) LENGTH |
| 9 | VERTEX_SUBNASAL VERTICAL LENGTH | 32 | INTER-TRAGUS VERTEX (ARC) LENGTH |
| 10 | VERTEX NOSE TIP VERTICAL LENGTH | 33 | INTER-TRAGUS MENTUM (ARC) LENGTH |
| 11 | VERTEX ROOT OF NOSE VERTICAL LENGTH | 34 | INTER-TRAGUS ROOT OF NOSE (ARC) LENGTH |
| 12 | VERTEX GLABELLA VERTICAL LENGTH | 35 | INTER-TRAGUS SUBNASAL (ARC) LENGTH |
| 13 | ROOT OF NOSE MENTUM VERTICAL LENGTH | 36 | LATERAL NECK VERTEX LATERAL NECK LENGTH |
| 14 | VERTEX RIGHT CROW VERTICAL LENGTH | 37 | HEAD WIDTH |
| 15 | VERTEX LEFT CROW VERTICAL LENGTH | 38 | INTER-CROW WIDTH |
| 16 | ROOT OF NOSE SUBNASAL VERTICAL LENGTH | 39 | INTER-PUPIL WIDTH |
| 17 | SUBNASAL MENTUM VERTICAL LENGTH | 40 | INTER-INNER CORNER OF EYE WIDTH |
| 18 | GLABELLA OCCIPUT PROTRUSION HORIZONTAL LENGTH | 41 | INTER-AURICLE WIDTH |
| 19 | RIGHT CROW OCCIPUT PROTRUSION HORIZONTAL LENGTH | 42 | INTER-TRAGUS WIDTH |
| 20 | LEFT CROW OCCIPUT PROTRUSION HORIZONTAL LENGTH | 43 | NOSE WIDTH |
| 21 | GLABELLA TRAGUS HORIZONTAL LENGTH | 44 | MOUTH WIDTH |
| 22 | NOSE TIP OCCIPUT PROTRUSION HORIZONTAL LENGTH | 45 | INTER-LOWER JAW WIDTH |
| 23 | MOUTH CENTERED OCCIPUT PROTRUSION HORIZONTAL LENGTH | | |

| | | HEAD CIRCUMFERENCE (1) -> 10<br>GLABELLA VERTEX OCCIPUT(ARC) LENGTH (2) -> 15<br>INTER-TRAGUS VERTEX (ARC) LENGTH(3) -> 15<br>VERTEX_LEFT TRAGION VERTICAL LENGTH(4) -> 5<br>LEFT CROW OCCIPUT PROTRUSION HORIZONTAL LENGTH(5) -> 17<br>INTER-TRAGUS WIDTH(6) -> 14 |
|---|---|---|
| [VALUES OF ITEMS TO BE COMPARED]<br>1-530, 2-288, 3-359<br>4-134, 5-152, 6-104 | [VALUES OF ITEMS TO BE COMPARED]<br>1-540, 2-263, 3-344<br>4-129, 5-169, 6-118 | |
| THREE-DIMENSIONAL HEAD SHAPE MEASUREMENT DATA OF SUBJECT A | THREE-DIMENSIONAL HEAD SHAPE OPTIMAL DATA GENERATED BY APPLYING GOLDEN RATIO OF FIBONACCI SEQUENCE FOR SUBJECT A | RESULT VALUE (DIFFERENCE VALUE) OBTAINED BY COMPARATIVELY ANALYZING THREE-DIMENSIONAL HEAD SHAPE MEASUREMENT DATA AND THREE-DIMENSIONAL OPTIMAL HEAD SHAPE DATA FOR SUBJECT A |

FIG. 11

| [VALUES OF ITEMS TO BE COMPARED]<br>1-569, 2-290, 3-383<br>4-136, 5-166, 6-116 | [VALUES OF ITEMS TO BE COMPARED]<br>1-540, 2-263, 3-344<br>4-129, 5-169, 6-118 | HEAD CIRCUMFERENCE (1) -> 29<br>GLABELLA VERTEX OCCIPUT(ARC) LENGTH (2) -> 29<br>INTER-TRAGUS VERTEX (ARC) LENGTH(3) -> 29<br>VERTEX_LEFT TRAGION VERTICAL LENGTH(4) -> -7<br>LEFT CROW OCCIPUT PROTRUSION HORIZONTAL LENGTH(5) -> 3<br>INTER-TRAGUS WIDTH(6) -> -6 |
|---|---|---|
| THREE-DIMENSIONAL HEAD SHAPE MEASUREMENT DATA OF SUBJECT B | THREE-DIMENSIONAL HEAD SHAPE OPTIMAL DATA GENERATED BY APPLYING GOLDEN RATIO OF FIBONACCI SEQUENCE FOR SUBJECT B | RESULT VALUE (DIFFERENCE VALUE) OBTAINED BY COMPARATIVELY ANALYZING THREE-DIMENSIONAL HEAD SHAPE MEASUREMENT DATA AND THREE-DIMENSIONAL OPTIMAL HEAD SHAPE DATA FOR SUBJECT B |

FIG. 12

| | | HEAD CIRCUMFERENCE (1) -> -16<br>GLABELLA VERTEX OCCIPUT(ARC) LENGTH (2) -> -22<br>INTER-TRAGUS VERTEX (ARC) LENGTH(3) -> -35<br>VERTEX_LEFT TRAGION VERTICAL LENGTH(4) -> -6<br>LEFT CROW OCCIPUT PROTRUSION HORIZONTAL LENGTH(5) -> 13<br>INTER-TRAGUS WIDTH(6) -> -16 |
|---|---|---|
| [VALUES OF ITEMS TO BE COMPARED]<br>1-556, 2-285, 3-379<br>4-135, 5-156, 6-134 | [VALUES OF ITEMS TO BE COMPARED]<br>1-540, 2-263, 3-344<br>4-129, 5-169, 6-118 | |
| THREE-DIMENSIONAL HEAD SHAPE MEASUREMENT DATA OF SUBJECT C | THREE-DIMENSIONAL HEAD SHAPE OPTIMAL DATA GENERATED BY APPLYING GOLDEN RATIO OF FIBONACCI SEQUENCE FOR SUBJECT C | RESULT VALUE (DIFFERENCE VALUE) OBTAINED BY COMPARATIVELY ANALYZING THREE-DIMENSIONAL HEAD SHAPE MEASUREMENT DATA AND THREE-DIMENSIONAL OPTIMAL HEAD SHAPE DATA FOR SUBJECT C |

FIG. 13

PERSONALIZED OPTIMAL HEAD SHAPE IMPLEMENTATION SYSTEM

TECHNICAL FIELD

The present invention relates to a personalized optimal head shape implementation system, and more particularly, to a personalized optimal head shape implementation system capable of deriving an optimal spline curve between head shape measurement data generated by scanning a head shape of a subject and optimal head shape data generated by applying a golden ratio of a Fibonacci sequence to the head shape measurement data.

BACKGROUND ART

In general, correcting a congenitally deformed head shape or cosmetically correcting a head shape has been made by a medical procedure. In this case, however, the medical procedure is not only a very difficult correction procedure, but is costly.

For this purpose, there is a need to correct a head shape by separate auxiliary tools.

However, when the auxiliary tools generally produced without being customized to each subject are used, the wearing sensation of the auxiliary tools is unpleasant, and thus the effect of the auxiliary tools is insignificant.

In recent years, customized auxiliary tools have been produced by converting images obtained by photographing a head shape using a CAD/CAM program or the like into data. In this case, however, the customized auxiliary tools typically have a form to fill dented parts. Most of them are not suitable to cosmetically correct a normal head shape.

On the other hand, the personalized optimal head shape implementation system according to the present invention may derive an optimal spline curve between head shape measurement data of a subject and optimal head shape data generated by applying a golden ratio of a Fibonacci sequence to the head shape measurement data and display a customized optimal head shape model of the subject reflecting the optimal spline curve through a separate device.

In this regard, Korean Patent No. 10-0645976 ("Pillow Customizing System") discloses a measurement system capable of providing a pillow tailored most suitably to head shape data obtained by measuring a flexural shape of a subject's head part.

RELATED ART DOCUMENT

Patent Document

Korean Patent No. 10-0645976 (Registration Date: Nov. 7, 2006)

DISCLOSURE

Technical Problem

An object of the present invention is to provide a personalized optimal head shape implementation system capable of deriving an optimal spline curve between head shape measurement data generated by scanning a head shape of a subject and optimal head shape data generated by applying a golden ratio of a Fibonacci sequence to the head shape measurement data.

However, an object of the present invention is not limited to the object described above, and other objects that are not stated may be clearly understood by those skilled in the art from the following description.

Technical Solution

In one general aspect, a personalized optimal head shape implementation system includes: a head shape scanner 100 generating head shape measurement data by scanning a head shape of a subject; a head shape implementer 200 generating optimal head shape data by applying a golden ratio of a Fibonacci sequence to the head shape measurement data of the subject generated by the head shape scanner 100; a head shape analyzer 300 deriving an optimal spline curve between the head shape measurement data and the optimal head shape data using a preset control point; and a display 400 displaying a customized optimal head shape to the subject using the optimal spline curve derived from the head shape analyzer 300, wherein the head shape implementer 200 applies the golden ratio of the Fibonacci sequence to the head shape measurement data so that a ratio of a nose length and a root of nose subnasal vertical length, a ratio of a procerus tragus horizontal length and the nose length, a root of nose auricle radix superior horizontal length and the nose length, a ratio of a vertex_right tragion vertical length and the root of nose auricle radix superior horizontal length, a ratio of a vertex_left tragion vertical length and the procerus tragus horizontal length, a ratio of the procerus tragus horizontal length and the vertex_left tragion vertical length, a ratio of a head vertical length and a vertex_right tragion vertical length, and a ratio of an inter-tragus vertex (arc) length and the head vertical length in the head shape measurement data each have the golden ratio of the Fibonacci sequence.

The head shape scanner 100 may be a contact type measuring device having a robot arm shape and may scan the head shape of the subject corresponding to a preset measuring point to generate the head shape measurement data.

The head shape analyzer 300 may preset a control point related to a side surface shape of the head shape and derive the optimal spline curve based on values corresponding to the respective control points between the head shape measurement data and the optimal head shape data.

Advantageous Effects

As described above, according to the personalized optimal head shape implementation system of the exemplary embodiment of the present invention, the optimal spline curve between the head shape measurement data generated by scanning the head shape of the subject and the optimal head shape data generated by applying the golden ratio of the Fibonacci sequence to the head shape measurement data can be derived and the customized optimal head shape for the subject based on the optimal spline curve can be displayed and transferred In addition, the optimal spline curve generated by applying the golden ratio of the Fibonacci sequence based on the head shape of the subject can be confirmed in real time to derive the optimal head shape.

BRIEF DESCRIPTION OF THE DRAWINGS

FIG. 4 is a diagram illustrating 45 measurement items configuring three-dimensional head shape measurement data used to scan the head shape of the subject in the present invention.

BEST MODE

Hereinafter, a personalized optimal head shape implementation system according to an exemplary embodiment of the present invention will be described in detail with reference to the accompanying drawings. The following introduced drawings are provided by way of example so that the idea of the present invention can be sufficiently transferred to those skilled in the art to which the present invention pertains. Therefore, the present invention is not limited to the accompanying drawings to be provided below, but may be implemented in other forms. In addition, like reference numerals denote like elements throughout the specification.

Technical terms and scientific terms used in the present specification have the general meaning understood by those skilled in the art to which the present invention pertains unless otherwise defined, and a description for the known function and configuration unnecessarily obscuring the gist of the present invention will be omitted in the following description and the accompanying drawings.

In addition, the system means a set of components including apparatuses, mechanisms, units, etc. which are organized and regularly interact with each other to perform required functions.

Figure 1:
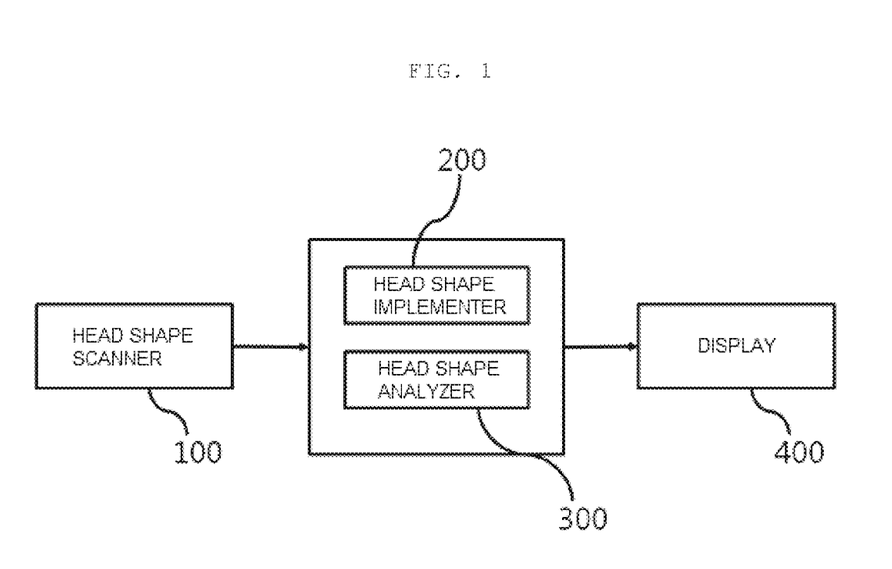
FIG. 1 is a diagram illustrating a personalized optimal head shape implementation system according to an exemplary embodiment of the present invention.
Figure 2:
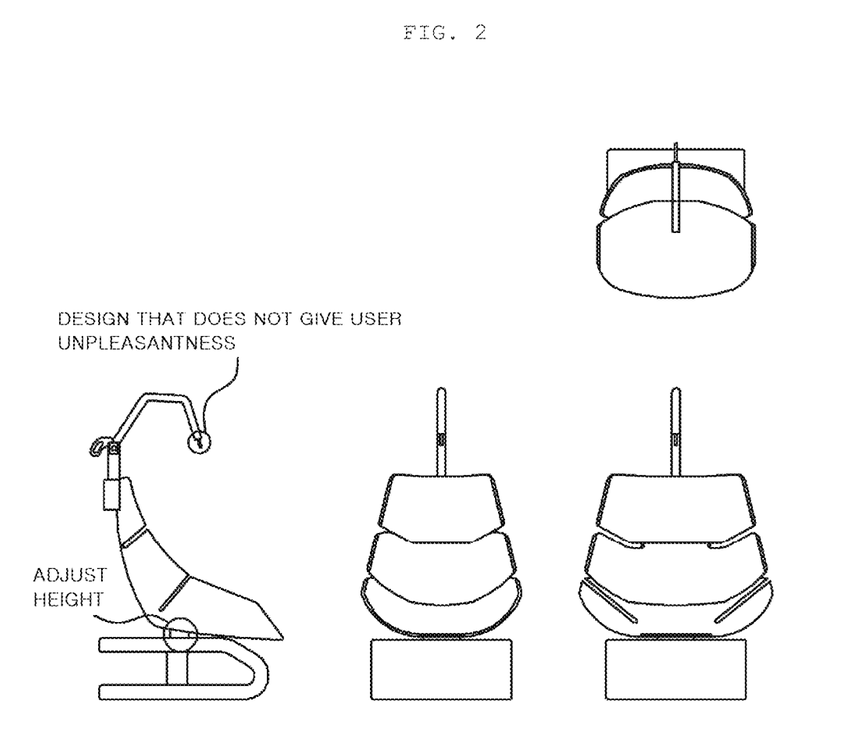
FIGS. 2 and 3 are diagrams illustrating a head shape measuring device used to scan a head shape of a subject in the personalized optimal head shape implementation system according to the exemplary embodiment of the present invention.
Figure 3:
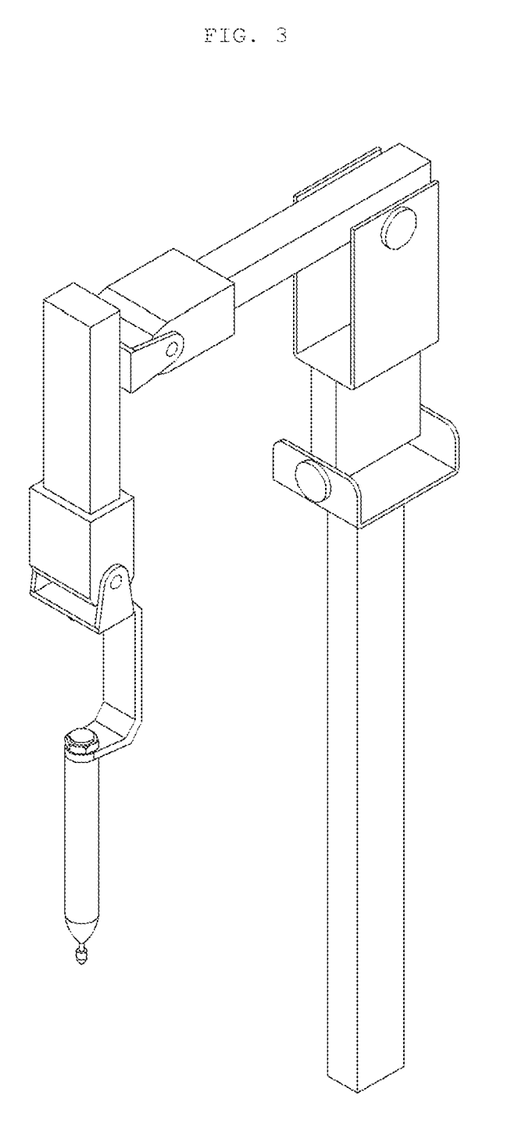
Figure 5:
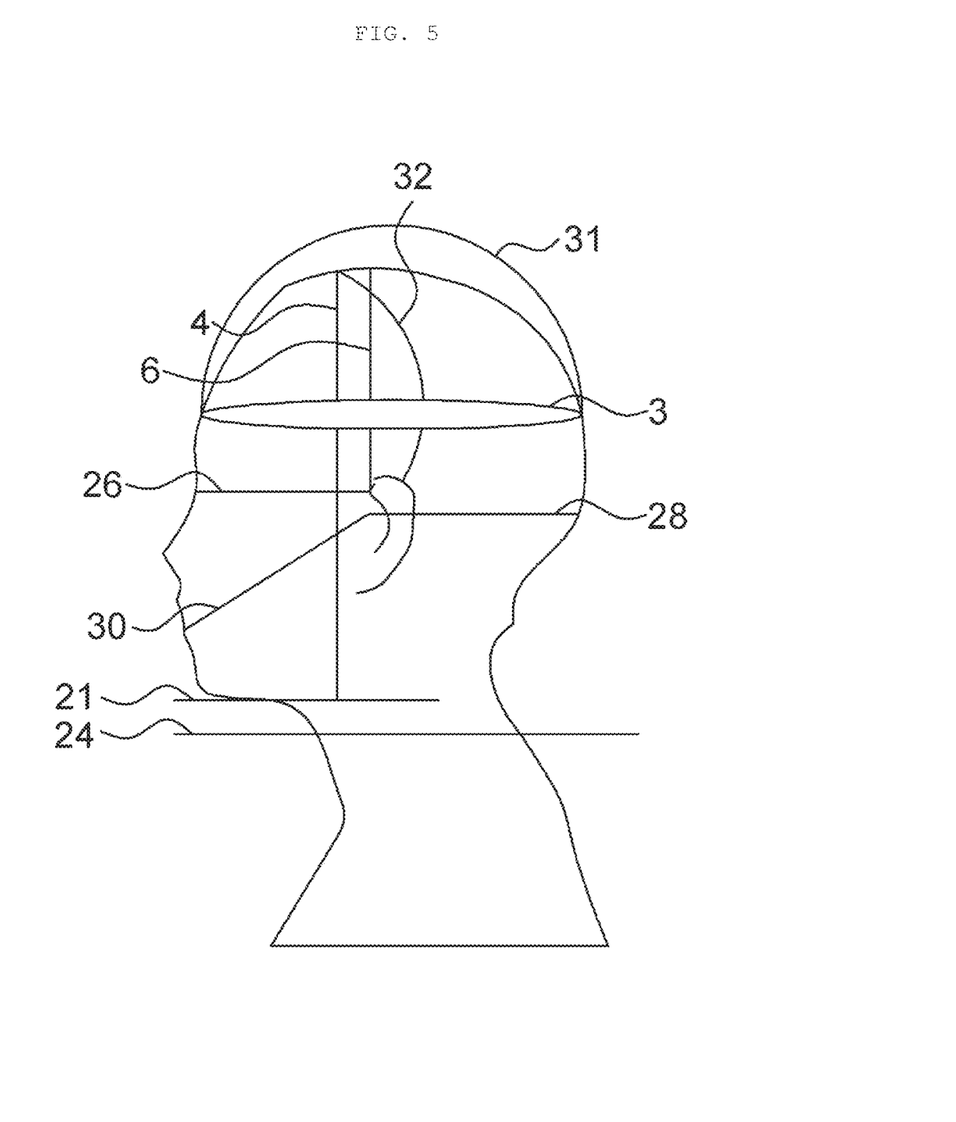
FIG. 5 is a diagram illustrating main items necessary for shaping a side surface of the head shape.
Figure 6:
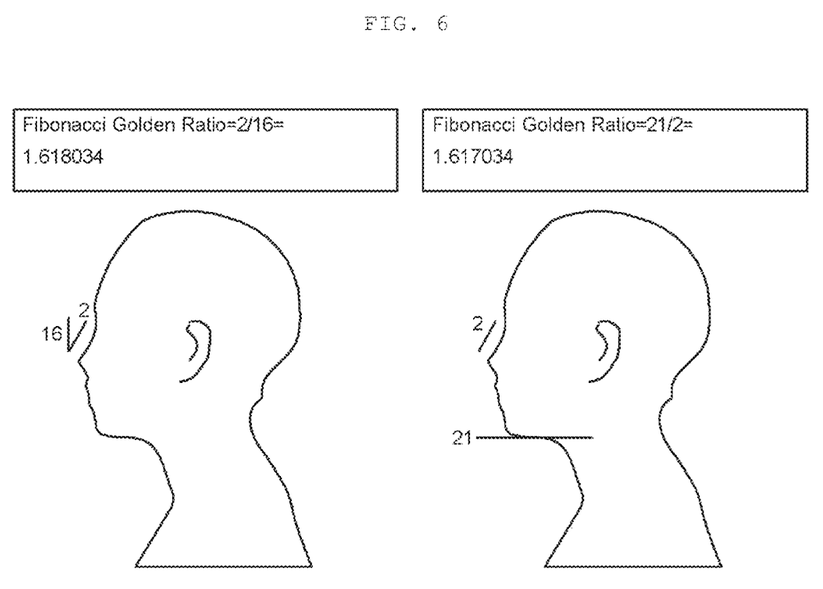
FIGS. 6 to 9 are diagrams illustrating a method of applying a golden ratio of a Fibonacci sequence to a side surface of a head shape.
Figure 7:
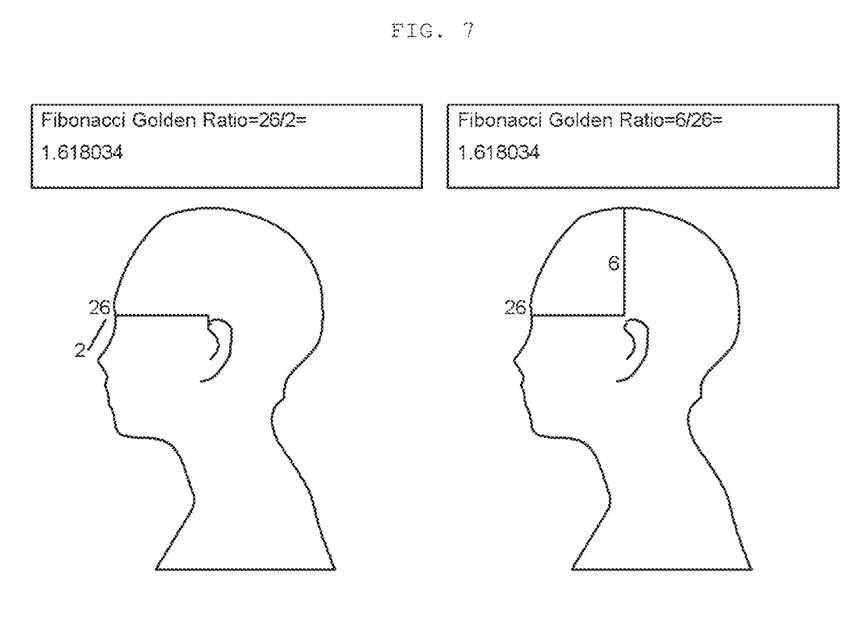
Figure 8:
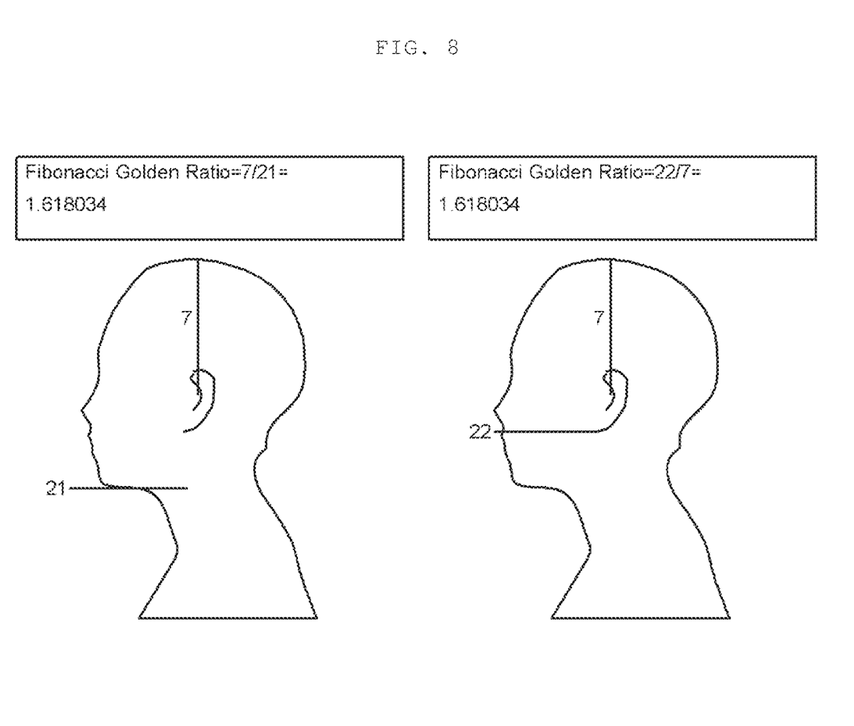
Figure 9:
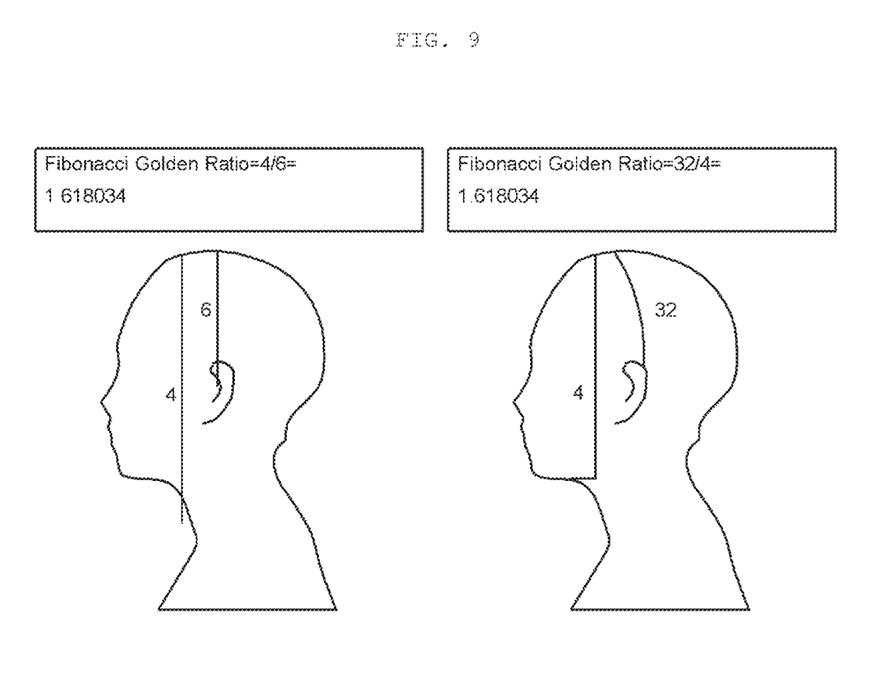
Figure 10:
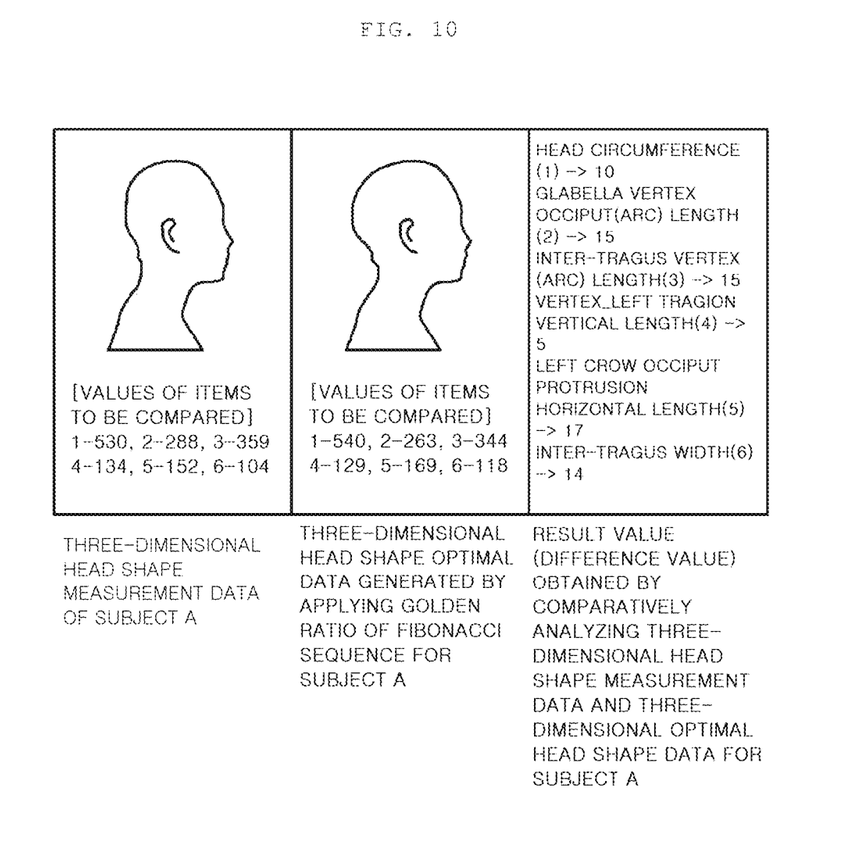
FIGS. 10 to 12 are diagrams illustrating an example of results of a comparative analysis between the three-dimensional head shape measurement data obtained by scanning the head shape of the subject and three-dimensional optimal head shape data obtained by applying the golden ratio of the Fibonacci sequence according to the personalized optimal head shape implementation system of the exemplary embodiment of the present invention.
Figure 11:
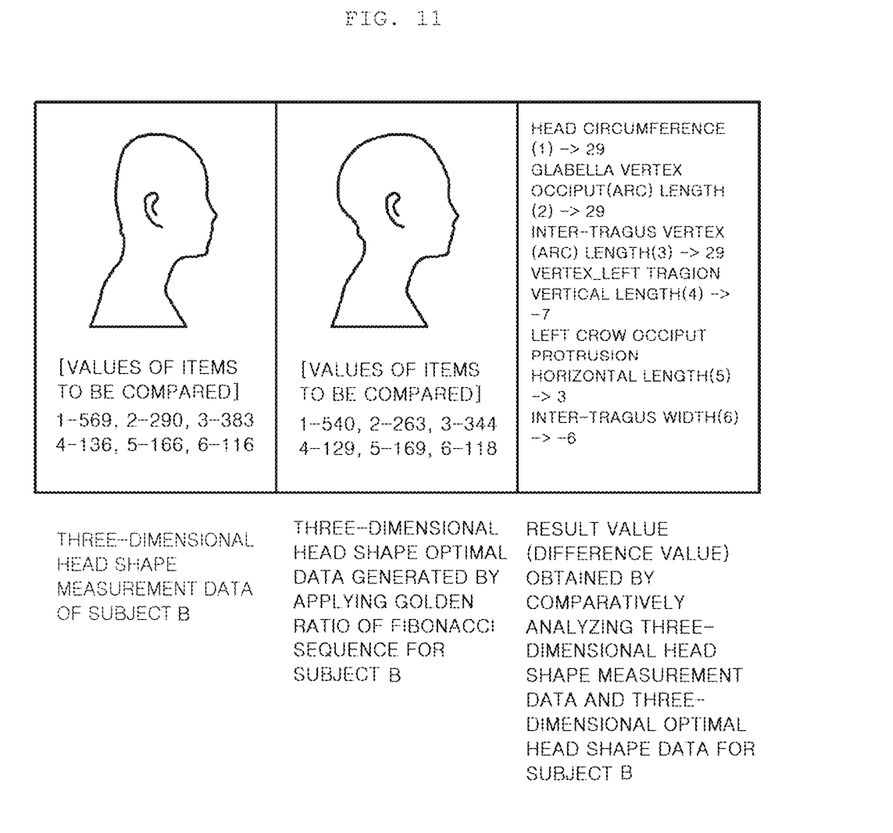
Figure 12:
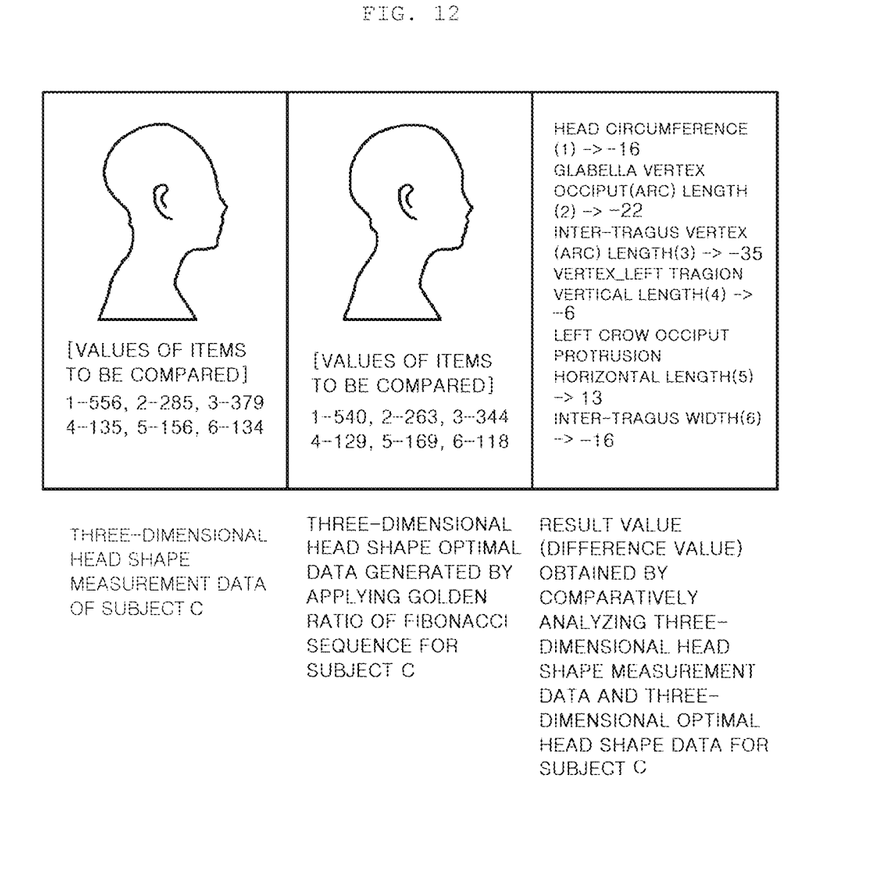
Figure 13:
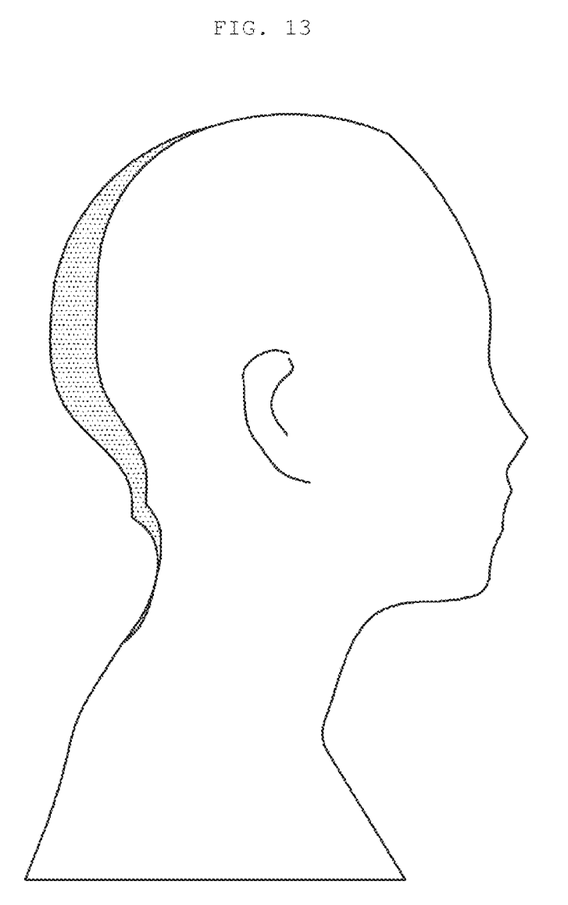
FIG. 13 is a diagram illustrating another example of results of a comparative analysis between the three-dimensional head shape measurement data obtained by scanning the head shape of the subject and the three-dimensional optimal head shape data obtained by applying the golden ratio of the Fibonacci sequence according to the personalized optimal head shape implementation system of the exemplary embodiment of the present invention.

FIG. 1 is a diagram illustrating a personalized optimal head shape implementation system according to an exemplary embodiment of the present invention, FIGS. 2 and 3 are diagrams illustrating a head shape measuring device used to scan a head shape of a subject in the personalized optimal head shape implementation system according to the exemplary embodiment of the present invention, FIG. 4 is a diagram illustrating 45 measurement items configuring three-dimensional head shape measurement data used to scan the head shape of the subject in the present invention, FIG. 5 is a diagram illustrating main items necessary for shaping a side surface of the head shape, FIGS. 6 to 9 are diagrams illustrating a method of applying a golden ratio of a Fibonacci sequence to a side surface of a head shape, FIGS. 10 to 12 are diagrams illustrating an example of results of a comparative analysis between the three-dimensional head shape measurement data obtained by scanning the head shape of the subject and three-dimensional optimal head shape data obtained by applying the golden ratio of the Fibonacci sequence according to the personalized optimal head shape implementation system of the exemplary embodiment of the present invention, and FIG. 13 is a diagram illustrating another example of results of a comparative analysis between the three-dimensional head shape measurement data obtained by scanning the head shape of the subject and the three-dimensional optimal head shape data obtained by applying the golden ratio of the Fibonacci sequence according to the personalized optimal head shape implementation system of the exemplary embodiment of the present invention.

Hereinafter, preferred embodiments of the present invention will be described in detail with reference to the accompanying drawings.

As illustrated in FIG. 1, the personalized optimal head shape implementation system according to the exemplary embodiment of the present invention includes a head shape scanner 100, a head shape implementer 200, a head shape analyzer 300, and a display 400.

The head shape scanner 100 preferably includes a measuring device for scanning a head shape of a subject, and the display 400 may be configured to include a monitor for displaying a customized optimal head shape model for a subject, and the like so that the subject and a measurer can see the customized optimal head shape model.

The head shape implementer 200 and the head shape analyzer 300 are preferably executed (executed by a statistical analysis program executed by an arithmetic processor including a computer) on software. By doing so, a subject can not only confirm optimal head shape data obtained by applying a Fibonacci sequence to measured head shape data in real time, but also easily confirm an optimal spline curve thus derived, thereby providing a customized optimal head shape mold.

Each component will be described in detail.

The head shape scanner 100 may generate the head shape measurement data by scanning the head shape of the subject. At this time, it is preferable to use a head measuring device for scanning the head shape of the subject.

As illustrated in FIGS. 2 and 3, the head shape measuring device is most preferably a contact type measuring device having a robot arm shape, and may generate the head shape measurement data by scanning the head shape of the subject corresponding to a preset measuring point.

More specifically, the head shape measuring device may generate the head shape measurement data while moving in east/west/south/north directions with respect to a center of the head shape in order to scan the head shape of the subject corresponding to the preset measuring point.

As illustrated in FIGS. 2 and 3, the head shape measuring device of the head shape scanner 100 according to the exemplary embodiment of the present invention is limited to the contact type measuring device having the robot arm shape, which is only one exemplary embodiment of the present invention. Accordingly, all the measuring devices capable of scanning the part corresponding to the measuring point which is preset in the head shape of the subject may generate the desired head shape measurement data.

As shown in FIG. 4, the head shape measurement data may include data of 45 head shape scan measurement items.

A factor analysis of the data of the 45 head shape scan measurement items may be performed for each subject and the personalized head shape measurement data of the subject may be generated using the factors extracted from the factor analysis for each subject.

Here, the factor analysis is for identifying factors that may not be directly measured based on a series of measured variables, and for simplifying the contents by bundling a number of variables into a few factors. In other words, the factor analysis may be used for the following purposes. First, several related variables are bundled into one factor, so many variables are reduced to a small number of factors. Second, it is possible to find variables with low importance even if they are not included in the factor. Therefore, unnecessary variables may be removed. Third, the related variables are bundled together to form the factors. These factors have mutually independent characteristics, so the characteristics of the variables may be investigated. Fourth, to measure one characteristic, the measured variables are bundled into one factor. Fifth, variables which may be used for regression analysis, discrimination analysis, cluster analysis, and the like which are additional analyses may be generated based on factorial discretion.

It is preferable to derive four main factors as shown in the following Table 1 by performing the factor analysis for generating the head shape measurement data in the head shape scanner 100 of the personalized optimal head shape implementation system according to the exemplary embodiment of the present invention.

TABLE 1

| | |
|---|---|
| Factor 1 | Length factor (vertex_lower jaw bone vertical length, vertex_right tragion vertical length, vertex_subnasal vertical length, vertex procerus vertical length, etc.) |
| Factor 2 | Head depth factor (subnasal mentum vertical length, subnasal occiput protrusion horizontal length, mentum occiput protrusion horizontal length, root of nose occiput protrusion horizontal length, etc.) |
| Factor 3 | Width factor (procerus tragus horizontal length, root of nose occiput protrusion horizontal length, crow tragus horizontal length, tragus lip linear length, etc.) |
| Factor 4 | Face factor (inter-tragus mentum (arc) length, inter-tragus subnasal (arc) length, inter-tragus width, etc.) |

The factor analysis of the personalized optimal head shape implementation system according to the exemplary embodiment of the present invention may be performed through statistical package for the social sciences (SPSS®) which is developed for data management and statistical analysis as an example.

The head shape implementer 200 may generate the optimal head shape data by applying the golden ratio of the Fibonacci sequence to the head shape measurement data of the subject generated by the head shape scanner 100.

The Fibonacci sequence is a sequence generated by Leonardo Fibonacci who is an Italian mathematician, and means a sequence which is expanded to values of the following terms by beginning with first and second terms as 1 and adding the last two terms.

This will be represented by the following equations.

$$f_1 = f_2 = 1$$

$$f_n = f_{n-2} + f_{n-1} (n \geq 3, \text{integer})$$

Describing the features of the Fibonacci sequence, the ratio of the first and second terms is 1/1=1, the ratio of the second and third terms is 1/2=0.5, and the ratio of the third and fourth terms is 2/3=0.667.

In this way, it is expanded to infinity and this ratio converges to $$\frac{\sqrt{5} - 1}{2} = 0.61803.$$

This value is referred to as the golden ratio (GR), which is represented by the following equation.

$$GR = \frac{-1 + \sqrt{5}}{2}$$

The golden ratio may be obtained based on the concept of the limit.

Here, the reciprocal number of the convergence value 0.61803 is represented by the following equation.

$$\frac{2}{\sqrt{5} - 1} = 1.61803$$

This has exactly a difference of 1, which means that the ratio of the reciprocal numbers of the respective terms converges to 1.61803, that is, means that the ratio of 1:0.61803 or 0.61803:1 becomes the golden ratio.

A rectangle and a curved line of the golden ratio may be drawn using the Fibonacci sequence. Here, if squares of which a length of one side is formed of each term of the Fibonacci sequence are drawn to be continuously adjacent to each other, a rectangle of the golden ratio having an aspect ratio of 1:0.61803 or 0.61803:1 is drawn, and if arcs exactly matching each square are drawn to be connected to each other, a curved line having a certain shape is drawn, such that a curved line of an actual ammonite shell is formed to have the golden ratio as above.

The personalized optimal head shape implementation system according to an exemplary embodiment of the present invention is applied to a generation of length values for each section required for shaping the head shape having the golden ratio of the Fibonacci sequence to generate data for the head shape having the golden ratio, i.e., the head shape measurement data.

FIG. 5 is a graphical representation of the main items required for shaping, in particular, the side surface of the head shape, among the 45 head shape scan measurement items of the head shape measurement data shown in FIG. 4. According to the exemplary embodiment of the present invention, as in the exemplary embodiments illustrated in FIGS. 6 to 9, the golden ratio of the Fibonacci sequence is applied to generate the length values for each section of the head shape including each item illustrated in FIG. 5.

That is, as illustrated in FIGS. 6 to 9, the head shape implementer 200 of the personalized optimal head shape implementation system according to the exemplary embodiment of the present invention may generate the length values for each section of the optimal head shape data generated by applying the golden ratio of the Fibonacci sequence and generate the head shape shaped based on the generated length values.

The head shape analyzer 300 may derive the optimal spline curve between the head shape measurement data and the optimal head shape data.

In detail, the head shape analyzer 300 may preset control points related to the side surface shape of the head shape and derive the optimal spline curve between the head shape measurement data and the optimal head shape data using the values corresponding to each of the preset control points.

In other words, the head shape analyzer 300 uses the control points related to the side surface shape between the head shape measurement data and the optimal head shape data and connects between the values corresponding to each of the preset control points between the optimal head shape data generated by applying the golden ratio of the Fibonacci sequence and the head shape measurement data generated by scanning the head shape of the subject, thereby preferably deriving the optimal spline curve.

FIGS. 10 to 12 illustrate an exemplary embodiment of results of an optimal spline curve derived based on head shape scan data of various subjects. As shown in FIGS. 10 to 12, the preset comparison target items may include a head circumference, a procerus vertex occiput (arc) length, an inter-tragus vertex (arc) length, a vertex_left tragion vertical length, a left crow occiput protrusion horizontal length, and an inter-tragus width.

Accordingly, the head shape analyzer 300 may derive the optimal spline curve by connecting the control points between the head shape measurement data and the optimal head shape data in the values corresponding to the preset control points.

According to the results of the head shape analyzer 300, the display 400 may provide the optimal spline curve between the head shape measurement data and the optimal head shape data as the result data, and preferably store and manage the result data.

In addition, the display 400 may display the customized optimal head shape model for the subject based on the results by the head shape analyzer 300, that is, the optimal spline curve so that the subject and the measurer may easily confirm the customized optimal head shape model.

In addition, the display 400 may overlay and display the three-dimensional head shape measurement data generated by scanning the head shape of the subject and the three-dimensional optimal head shape data generated by applying the golden ratio of the Fibonacci sequence, that is, the customized optimal head shape model as illustrated in FIG. 13 based on the results by the head shape analyzer 300, that is, the optimal spline curve so that the subject easily performs the comparative analysis on the customized optimal head shape model at a glance.

Accordingly, it is possible to easily confirm the difference between the head shape measurement data and the optimal head shape data using the shape as well as the numerical value.

That is, the personalized optimal head shape implementation system according to the exemplary embodiment of the present invention performs the comparative analysis on the head shape measurement data generated by measuring the head shape of the subject and the optimal head shape data generated by applying the measured head shape measurement data to the golden ratio of the Fibonacci sequence, calculates the optimal spline curve between the head shape measurement data and the head shape measurement data as the result values using the control points, and applies the calculated result values to the software, thereby confirming the optimal spline curve of the subject in real time based on various embodiments.

Hereinabove, although the present invention has been described by specific matters such as detailed components, exemplary embodiments, and the accompanying drawings, they have been provided only for assisting in the entire understanding of the present invention. Therefore, the present invention is not limited to the exemplary embodiments. Various modifications and changes may be made by those skilled in the art to which the present invention pertains from this description.

Therefore, the spirit of the present invention should not be limited to these exemplary embodiments, but the claims and all of modifications equal or equivalent to the claims are intended to fall within the scope and spirit of the present invention.

DETAILED DESCRIPTION OF MAIN ELEMENTS

100: Head shape scanner
200: Head shape implementer
300: Head shape analyzer
400: Display

The invention claimed is:

1. A personalized optimal head shape implementation system, comprising:
   a head shape scanner configured to scan a head shape of a subject and generate head shape measurement data of the subject;
   a head shape implementer configured to apply a golden ratio of a Fibonacci sequence to the head shape measurement data of the subject generated by the head shape scanner to generate optimal head shape data, wherein the optimal head shape data comprises a plurality of ratios having the golden ratio of the Fibonacci sequence, wherein the plurality of ratios comprise:
      a ratio of a nose length and a vertical length between a root of a nose and a subnasal portion of the nose,
      a ratio of a horizontal length between a procerus and a tragus and the nose length
      a ratio of a horizontal length between the root of the nose and an auricle radix superior and the nose length,
      a ratio of a vertical length between a vertex and a right tragion and the horizontal length of the root of the nose and the auricle radix superior,
      a ratio of a vertical length between the vertex and a left tragion and the horizontal length between the procerus and the tragus,
      a ratio of the horizontal length between the procerus and the tragus and the vertical length between the vertex and the left tragion,
      a ratio of a vertical length of the head and the vertical length between the vertex and a right tragion, and
      a ratio of a length of an arc between an inter-tragus and the vertex, and the vertical length of the head;
   a head shape analyzer configured to preset control points related to the head shape and derive an optimal spline curve between the head shape measurement data and the optimal head shape data using the preset control points; and
   a display configured to display a customized optimal head shape for the subject using the optimal spline curve derived by the head shape analyzer,
   wherein the personalized optimal head shape implementation system is configured to form a customized optimal head shape article having a physical shape that is at least partially defined by the optimal spline curve.

2. The personalized optimal head shape implementation system of claim 1, wherein the head shape scanner is a contact type measuring device having a robot arm shape and scans the head shape of the subject to generate the head shape measurement data.

\* \* \* \* \*